*(12)* United States Patent
Do et al.

(10) Patent No.: US 8,195,406 B2
(45) Date of Patent: Jun. 5, 2012

(54) ESTIMATING CONSUMER STATUS USING NON-INVASIVE TECHNOLOGY

(75) Inventors: Lydia Mai Do, RTP, NC (US); Pamela Ann Nesbitt, Ridgefield, CT (US); Lisa Anne Seacat, San Francisco, CA (US)

(73) Assignee: International Business Machines Corporation, Armonk, NY (US)

( * ) Notice: Subject to any disclaimer, the term of this patent is extended or adjusted under 35 U.S.C. 154(b) by 594 days.

(21) Appl. No.: 12/327,172

(22) Filed: Dec. 3, 2008

(65) Prior Publication Data

US 2010/0138166 A1    Jun. 3, 2010

(51) Int. Cl.
*G01N 31/00* (2006.01)
(52) U.S. Cl. .......... 702/24; 702/173; 702/127; 702/101; 702/104; 73/23.3; 436/900
(58) Field of Classification Search ............... 702/24; 73/23.3; 439/900
See application file for complete search history.

(56) References Cited

U.S. PATENT DOCUMENTS

| 5,157,601 | A | * | 10/1992 | Jones et al. | 600/300 |
|---|---|---|---|---|---|
| 5,886,336 | A | * | 3/1999 | Tang et al. | 235/462.43 |
| 6,017,308 | A | * | 1/2000 | Fults | 600/300 |
| 6,261,239 | B1 | * | 7/2001 | Abraham-Fuchs et al. | 600/558 |
| 7,287,687 | B2 | * | 10/2007 | Vercnocke et al. | 235/375 |
| 2006/0180378 | A1 | * | 8/2006 | Nordin | 180/272 |
| 2006/0182661 | A1 | * | 8/2006 | Aquila | 422/84 |
| 2006/0231616 | A1 | * | 10/2006 | Gibault | 235/383 |
| 2006/0282344 | A1 | * | 12/2006 | Brown | 705/28 |
| 2006/0284874 | A1 |  | 12/2006 | Wilson | 345/473 |
| 2007/0239549 | A1 | * | 10/2007 | LaFauci et al. | 705/15 |
| 2008/0270324 | A1 | * | 10/2008 | Allard et al. | 705/400 |
| 2011/0252839 | A1 | * | 10/2011 | Stevens | 70/63 |

* cited by examiner

*Primary Examiner* — Drew A Dunn
*Assistant Examiner* — Timothy H Hwang
(74) *Attorney, Agent, or Firm* — VanLeeuwen & VanLeeuwen; Jeffrey S. LaBaw

(57) ABSTRACT

One or more alcohol inputs are received at the interactive system. Each of the alcohol inputs corresponds to an alcoholic beverage to be consumed by a consumer. The system calculates an estimated blood-alcohol level of the consumer based on the alcohol inputs. The estimated blood-alcohol level is compared with one or more alcohol impairment limits retrieved from an electronic data store. If the comparison reveals that the consumer might be impaired, an alert is automatically signaled.

17 Claims, 7 Drawing Sheets

ESTIMATING CONSUMER STATUS USING NON-INVASIVE TECHNOLOGY

BACKGROUND OF THE INVENTION

1. Technical Field

The present invention relates to a way of automatically and non-invasively estimating the amount of alcohol consumed by a consumer.

2. Description of the Related Art

Driving motor vehicles while impaired due to excessive alcohol consumption is a major problem in many areas. Patrons that consume alcohol may not realize the amount of alcoholic beverages that they have consumed. This lack of understanding, coupled with impairment and judgment deficiencies brought about by alcohol consumption, can lead a person to drive a vehicle from an establishment, such as a restaurant or pub, when they are legally impaired.

Some jurisdictions have addressed this issue by placing liability on the establishment that served the individual alcohol. While this shifts some of the responsibility, it often does result in establishments policing customers and cutting off customers that are over the limit. To abide by these laws, establishments traditionally rely on judgment of employees such as wait-staff, bartenders, servers, and the like. These employees are often poorly trained with respect to identifying customers over the limit. In addition, due to large number of customers at some establishments, these employees have a difficult time identifying which customers are driving as well as keeping track of how many drinks a particular customer has consumed. Exacerbating these challenges is the fact that simply keeping track of the number of drinks a customer has consumed does not result in a good measure of a customer's intoxication level without also keeping track of other factors related to the customer, such as the customer's weight and gender. Indeed, due to the effects of consuming too much alcohol, consumers' judgments may become impaired so that they forget how many drinks they have consumed and may also have a mistaken belief that they are sober enough to drive an automobile when, in fact, their driving ability may be impaired.

One approach that some establishments have used is to provide breathalyzers that, when used by a customer, provides a digital result of a customer's blood-alcohol limit. A challenge of this approach, however, is that it is quite invasive and may likely result in customers refusing to take the breathalyzer test or refraining from visiting the establishment, resulting in a loss of business, and revenue, for the establishment.

SUMMARY

It has been discovered that the aforementioned challenges are resolved using an interactive device that estimates a user's impairment in a non-invasive fashion. One or more alcohol inputs are received at the interactive system. Each of the alcohol inputs corresponds to an alcoholic beverage to be consumed by a consumer. The system calculates an estimated blood-alcohol level of the consumer based on the alcohol inputs. The estimated blood-alcohol level is compared with one or more alcohol impairment limits retrieved from an electronic data store. If the comparison reveals that the consumer might be impaired, an alert is automatically signaled.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings, wherein.

DETAILED DESCRIPTION

The following is intended to provide a detailed description of an example of the invention and should not be taken to be limiting of the invention itself. Rather, any number of variations may fall within the scope of the invention, which is defined in the claims following the description.

Certain specific details are set forth in the following description and figures to provide a thorough understanding of various embodiments of the invention. Certain well-known details often associated with computing and software technology are not set forth in the following disclosure, however, to avoid unnecessarily obscuring the various embodiments of the invention. Further, those of ordinary skill in the relevant art will understand that they can practice other embodiments of the invention without one or more of the details described below. Finally, while various methods are described with reference to steps and sequences in the following disclosure, the description as such is for providing a clear implementation of embodiments of the invention, and the steps and sequences of steps should not be taken as required to practice this invention. Instead, the following is intended to provide a detailed description of an example of the invention and should not be taken to be limiting of the invention itself. Rather, any number of variations may fall within the scope of the invention, which is defined by the claims that follow the description.

The following detailed description will generally follow the summary of the invention, as set forth above, further explaining and expanding the definitions of the various aspects and embodiments of the invention as necessary. To this end, this detailed description first sets forth a computing environment in FIG. 1 that is suitable to implement the software and/or hardware techniques associated with the invention. A networked environment is illustrated in FIG. 2 as an extension of the basic computing environment, to emphasize that modern computing techniques can be performed across multiple discrete devices.

Figure 1:
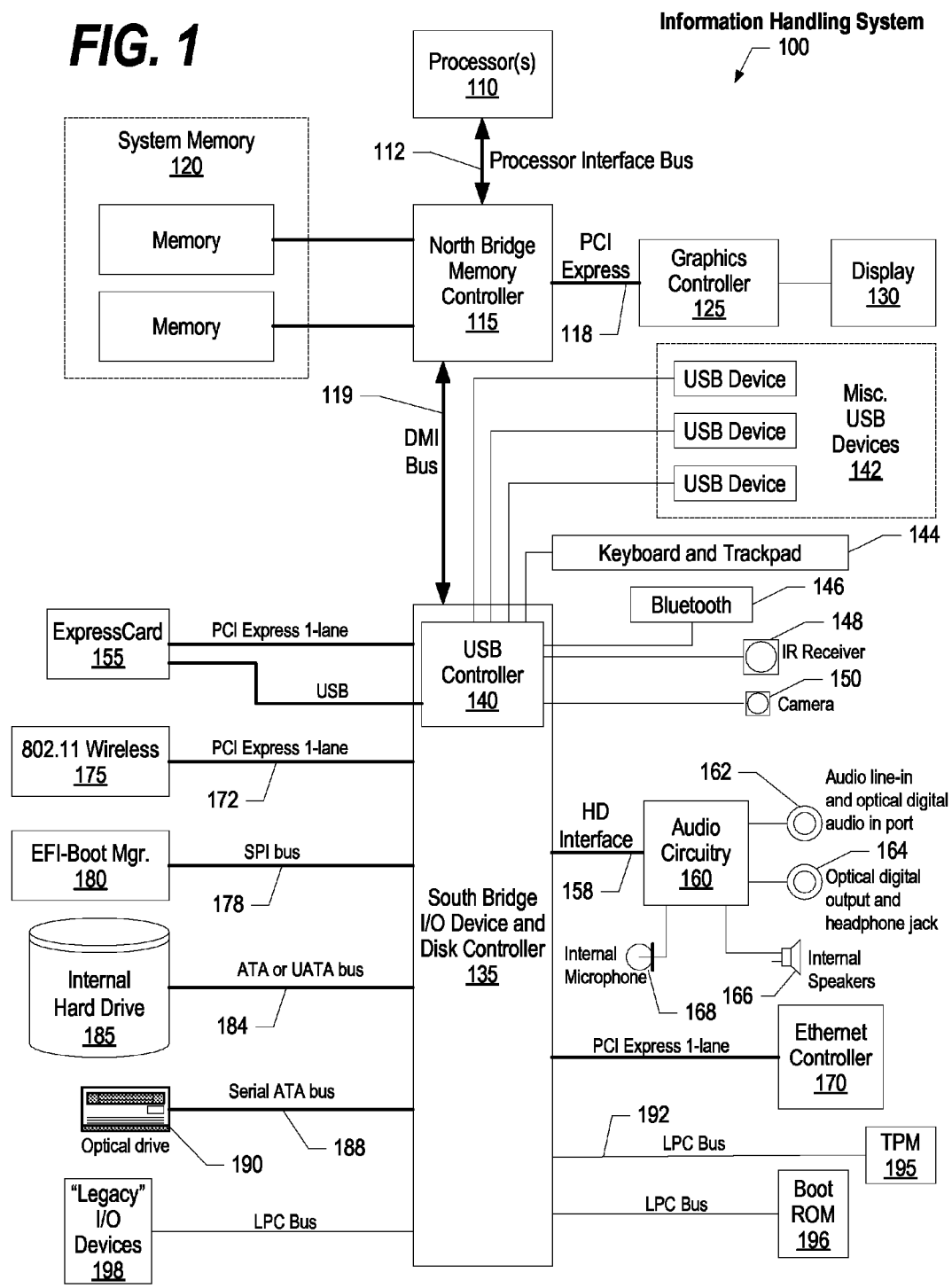
FIG. 1 is a block diagram of a data processing system in which the methods described herein can be implemented.
Figure 2:
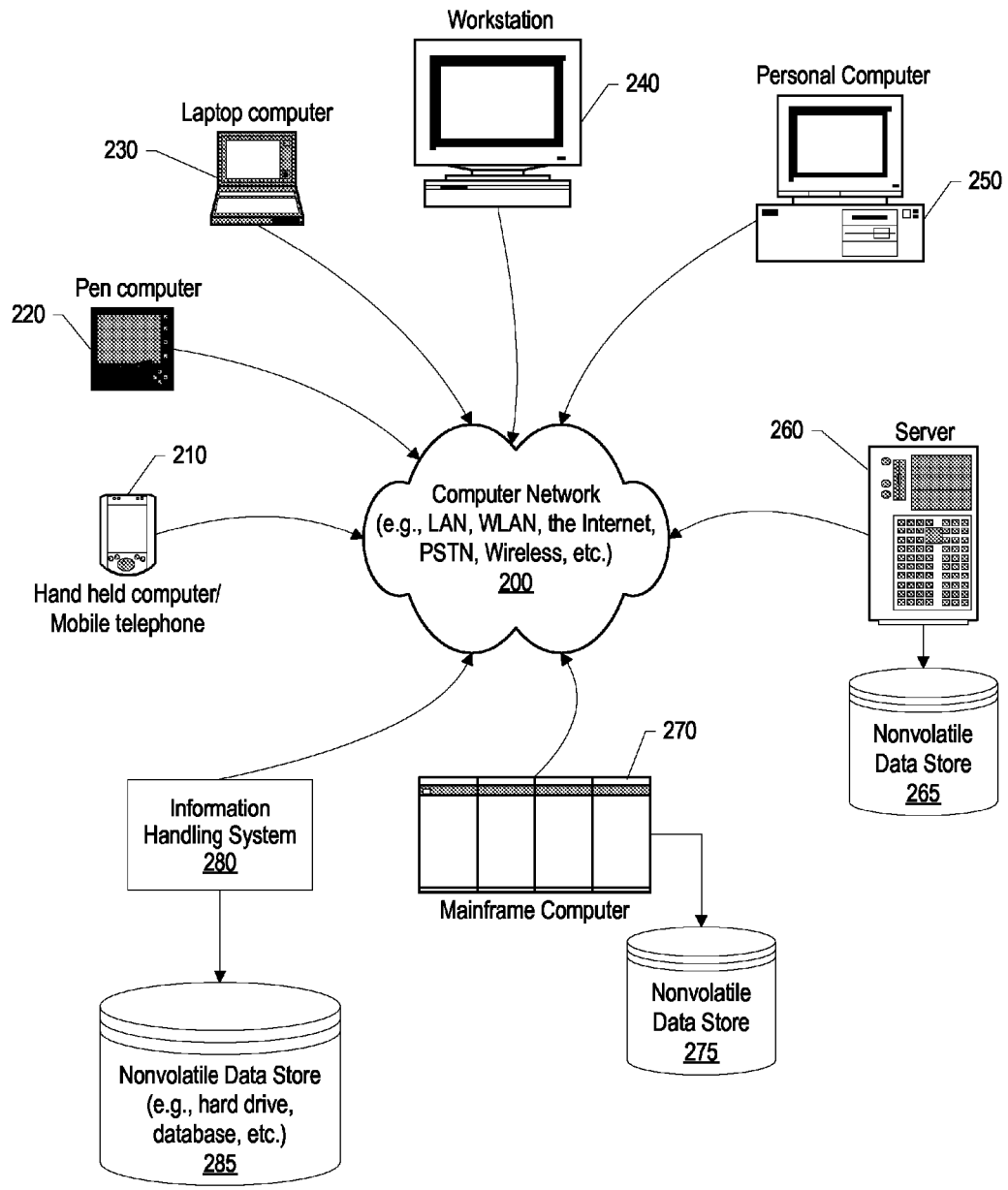
FIG. 2 provides an extension of the information handling system environment shown in FIG. 1 to illustrate that the methods described herein can be performed on a wide variety of information handling systems which operate in a networked environment.

FIG. 1 illustrates information handling system 100 which is a simplified example of a computer system capable of performing the computing operations described herein. Information handling system 100 includes one or more processors 110 which are coupled to processor interface bus 112. Processor interface bus 112 connects processors 110 to Northbridge 115, which is also known as the Memory Controller Hub (MCH). Northbridge 115 is connected to system memory 120 and provides a means for processor(s) 110 to access the system memory. Graphics controller 125 is also connected to Northbridge 115. In one embodiment, PCI Express bus 118 is used to connect Northbridge 115 to graphics controller 125. Graphics controller 125 is connected to display device 130, such as a computer monitor.

Northbridge 115 and Southbridge 135 are connected to each other using bus 119. In one embodiment, the bus is a Direct Media Interface (DMI) bus that transfers data at high speeds in each direction between Northbridge 115 and Southbridge 135. In another embodiment, a Peripheral Component Interconnect (PCI) bus is used to connect the Northbridge and the Southbridge. Southbridge 135, also known as the I/O Controller Hub (ICH) is a chip that generally implements capabilities that operate at slower speeds than the capabilities provided by the Northbridge. Southbridge 135 typically provides various busses used to connect various components. These busses can include PCI and PCI Express busses, an ISA bus, a System Management Bus (SMBus or SMB), a Low Pin Count (LPC) bus. The LPC bus is often used to connect low-bandwidth devices, such as boot ROM 196 and "legacy" I/O devices (using a "super I/O" chip). The "legacy" I/O devices (198) can include serial and parallel ports, keyboard, mouse, floppy disk controller. The LPC bus is also used to connect Southbridge 135 to Trusted Platform Module (TPM) 195. Other components often included in Southbridge 135 include a Direct Memory Access (DMA) controller, a Programmable Interrupt Controller (PIC), a storage device controller, which connects Southbridge 135 to nonvolatile storage device 300 such as a hybrid hard disk drive, using bus 184.

ExpressCard 155 is a slot used to connect hot-pluggable devices to the information handling system. ExpressCard 155 supports both PCI Express and USB connectivity as it is connected to Southbridge 135 using both the Universal Serial Bus (USB) the PCI Express bus. Southbridge 135 includes USB Controller 140 that provides USB connectivity to devices that connect to the USB. These devices include webcam (camera) 150, infrared (IR) receiver 148, Bluetooth device 146 which provides for wireless personal area networks (PANs), keyboard and trackpad 144, and other miscellaneous USB connected devices 142, such as a mouse, removable nonvolatile storage device 145, modems, network cards, ISDN connectors, fax, printers, USB hubs, and many other types of USB connected devices. While removable nonvolatile storage device 145 is shown as a USB-connected device, removable nonvolatile storage device 145 could be connected using a different interface, such as a Firewire interface, etc.

Wireless Local Area Network (LAN) device 175 is connected to Southbridge 135 via the PCI or PCI Express bus 172. LAN device 175 typically implements one of the IEEE 802.11 standards of over-the-air modulation techniques that all use the same protocol to wireless communicate between information handling system 100 and another computer system or device. Optical storage device 190 is connected to Southbridge 135 using Serial ATA (SATA) bus 188. Serial ATA adapters and devices communicate over a high-speed serial link. The Serial ATA bus is also used to connect Southbridge 135 to other forms of storage devices, such as hard disk drives. Audio circuitry 160, such as a sound card, is connected to Southbridge 135 via bus 158. Audio circuitry 160 is used to provide functionality such as audio line-in and optical digital audio in port 162, optical digital output and headphone jack 164, internal speakers 166, and internal microphone 168. Ethernet controller 170 is connected to Southbridge 135 using a bus, such as the PCI or PCI Express bus. Ethernet controller 170 is used to connect information handling system 100 with a computer network, such as a Local Area Network (LAN), the Internet, and other public and private computer networks.

While FIG. 1 shows one information handling system, an information handling system may take many forms. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

The Trusted Platform Module (TPM 195) shown in FIG. 1 and described herein to provide security functions is but one example of a hardware security module (HSM). Therefore, the TPM described and claimed herein includes any type of HSM including, but not limited to, hardware security devices that conform to the Trusted Computing Groups (TCG) standard, and entitled "Trusted Platform Module (TPM) Specification Version 1.2." The TPM is a hardware security subsystem that may be incorporated into any number of information handling systems, such as those outlined in FIG. 2.

FIG. 2 provides an extension of the information handling system environment shown in FIG. 1 to illustrate that the methods described herein can be performed on a wide variety of information handling systems which operate in a networked environment. Types of information handling systems range from small handheld devices, such as handheld computer/mobile telephone 210 to large mainframe systems, such as mainframe computer 270. Examples of handheld computer 210 include personal digital assistants (PDAs), personal entertainment devices, such as MP3 players, portable televisions, and compact disc players. Other examples of information handling systems include pen, or tablet, computer 220, laptop, or notebook, computer 230, workstation 240, personal computer system 250, and server 260. Other types of information handling systems that are not individually shown in FIG. 2 are represented by information handling system 280. As shown, the various information handling systems can be networked together using computer network 200. Types of computer network that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling system include nonvolatile data stores, such as hard drives and/or nonvolatile memory. Some of the information handling systems shown in FIG. 2 are depicted with separate nonvolatile data stores (server 260 is shown with nonvolatile data store 265, mainframe computer 270 is shown with nonvolatile data store 275, and information handling system 280 is shown with nonvolatile data store 285). The nonvolatile data store can be a component that is external to the various information handling systems or can be internal to one of the information handling systems. In addition, removable nonvolatile storage device 145 can be shared amongst two or more information handling systems using various techniques, such as connecting the removable nonvolatile storage device 145 to a USB port or other connector of the information handling systems.

Figure 3:
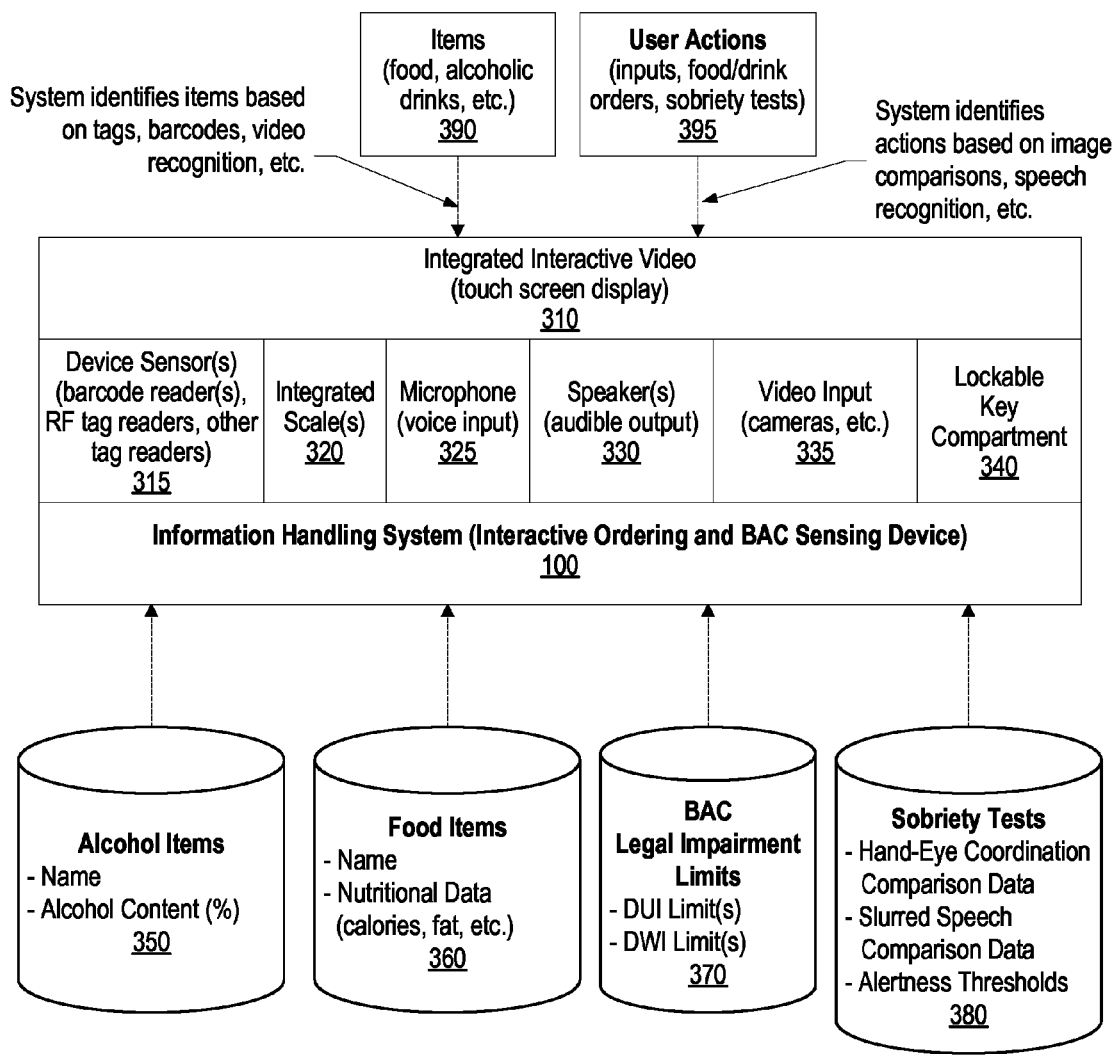
FIG. 3 is a diagram of the components used in an interactive device used to estimate consumer's alcohol intake with the interactive device being an extension of the information handling system shown in FIG. 1.

FIG. 3 is a diagram of the components used in an interactive device used to estimate consumer's alcohol intake with the interactive device being an extension of the information handling system shown in FIG. 1. Information handling system 100, which is an interactive device, includes integrated interactive video display 310 which is a touch screen display surface. In one embodiment, display 310 is mounted horizontally so that items 390, such as food and beverages (alcoholic and non-alcoholic beverages) can be placed upon the display. In a further embodiment, the horizontal display is a flexible surface (such as a Flexible Organic Light-Emitting Diode (Flexible OLED or FOLED) display panel). Device sensors 315 are included in the interactive device. The choice as to whether to have the interactive device estimate the consumer's alcohol intake is a voluntary choice made by the consumer in order to better understand how much alcohol the consumer has consumed over a period of time.

The interactive device is employed in establishments, such as nightclubs, restaurants, and bars, for voluntary use by the establishments' patrons. Voluntary use of the interactive device by patrons helps give a user a better understanding of how much alcohol the user has consumed at the establishment, and accordingly, whether the user ought to operate a motor vehicle or should instead seek another means of transportation, such as a taxi, bus, or subway.

In one embodiment, device sensors 315 are barcode sensors, in another embodiment the sensors are RF tag or other tag readers, and in another embodiment the sensors are a combination of barcode and tag reading sensors. Sensors 315 are used to sense various items 390 placed on horizontal surface 310. These items may include various implements (e.g., knives, spoons, etc.), food items (plates of food, bowls of food, etc), and beverage items (wine glasses filled with wine, beer mugs filled with beer, shot glasses with a shot of alcohol, mixed drink glasses with mixed drinks, non-alcohol beverage glasses, etc.). Items are affixed with an identifier, such as a barcode or a tag, that can be sensed by sensors 315 when the item is placed in proximity to one or more of the sensors. One or more integrated scales 320 are also included in the interactive device. Integrated scales 320 are used to weigh items 390 placed on the surface of the interactive device. In one embodiment, the interactive device includes microphone 325 to allow the user to communicate with the interactive device using voice responses and commands. As noted, one of user actions 395 include voice input that is received by microphone 325. One or more speakers 330 are included in the interactive device in order to provide the user with audible output, such as audible output used in recipe preparation. In addition, audible output from speakers 330 can be combined with multimedia content where a video is displayed on horizontal display screen 310 coupled with audio that is played through speakers 330.

Video input devices 335 are also included in the interactive device. Video input devices 335 can capture images of items 390 that are in proximity of the interactive device. In this manner, video input devices 335 can be used as additional sensor devices, especially when an item does not have an identifier and is, instead, identified based on the items shape or appearance using one or more video input devices. In addition, video input devices 335 capture user actions 395, such as the user performing a actions, making various gestures, and the like. Lockable key compartment 340 is controlled (locked, unlocked, etc.) by interactive device and provides a place for the user to voluntarily place vehicle keys while the user is at the establishment. As described in FIG. 7, the keys are unlocked by the interactive device upon checkout if the interactive device determines that the user's ability to drive a motor vehicle is not impaired.

Various data stores (e.g., databases, flat files, etc.) are stored in nonvolatile storage devices accessible from the interactive device 100. As shown, these data stores include alcohol data store 350 that includes the names of alcoholic beverages available and the alcohol content of the beverage. Food items data store 360 likewise contains the names of food items as well as the nutritional values associated with food items (e.g., non-alcoholic items, etc.). Blood-alcohol content (BAC) legal impairment limits data store 370 includes the impairment limits that have been set for the jurisdiction where the establishment is located. Some jurisdictions have more than one limit (e.g., a driving while impaired (DWI) limit as well as a driving under the influence (DUI) limit). In these jurisdictions the lowest limit (e.g., the DWI limit) or both limits would be included in data store 370. Sobriety tests data store 380 include data regarding sobriety tests that can be provided by interactive device 100. This data includes hand-eye coordination comparison data used to compare to the user's hand-eye test performance results in order to determine whether the user's hand-eye coordination performance appears impaired. Slurred speech comparison data is also included in data store 380 both to provide paragraphs that the user reads as well as comparison data to check to see if the user's speech appears slurred and, thus, the user could be impaired due to alcohol intake. Alertness threshold data is also included in data store 380 to provide comparison data to use to check if the user's alertness appears impaired (e.g., the time and accuracy the user should be able to add a series of small numbers, etc.)

Figure 4:
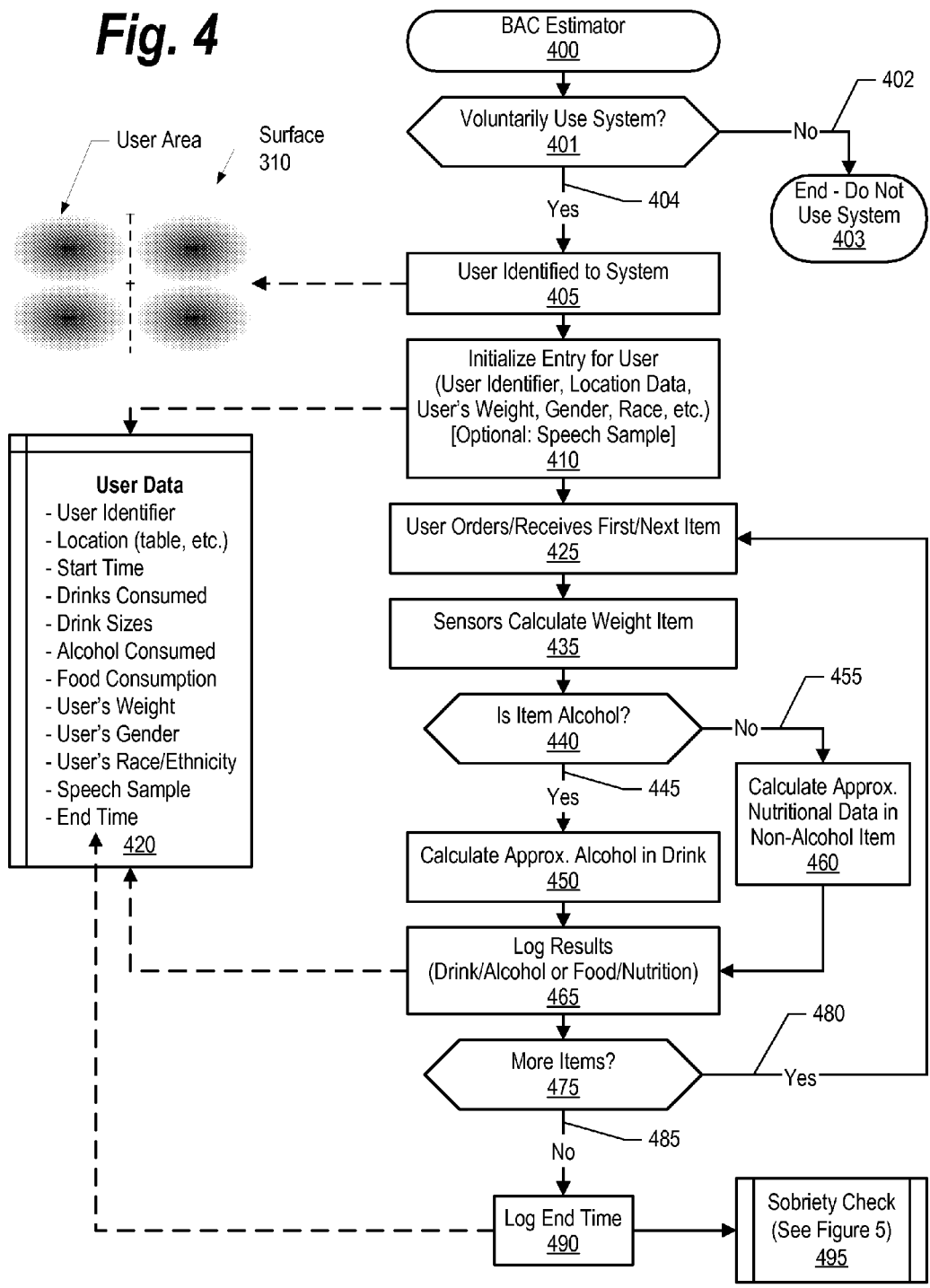
FIG. 4 is a flowchart showing steps taken using the device to estimate a consumer's blood-alcohol content in a non-intrusive manner.

FIG. 4 is a flowchart showing steps taken using the device to estimate a consumer's blood-alcohol content in a non-intrusive manner. Estimating the user's blood-alcohol content is a voluntary process that is voluntarily used by the user so that the user can assess the user's own blood-alcohol level. As a voluntary system, processing commences at 400 whereupon the first decision made (decision 401) is whether the consumer wishes to voluntarily use the system. If the user does not wish to use the system, then decision 401 branches to "no" branch 402 whereupon, at 403 processing ends and the system is not used to assist the user in keeping track of the user's alcohol intake.

On the other hand, if the user wants to voluntarily use the system, then decision 401 branches to "yes" branch 404 whereupon, at step 405, the consumer (user) is identified to the system using interactive device surface 310 using a variety of approaches such as scanning an identifier (e.g., driver's license, etc.), reading a biometric input (e.g., fingerprint, retina scan, etc.), or manually inputting the user's identification using a traditional input device, such as a keyboard.

At step 410, an entry is initialized in user data store 420. Initialization of the user's record, in one embodiment, is performed once and then retrieved upon subsequent visits by the user. In addition, an electronic key, such as a smart card or USB storage device, can be used as a user's portable data holder so that the user does not need to input the user's data at each establishment visited by the user. In addition, a computer network, such as computer network 200 shown in FIG. 2 (e.g., the Internet, etc.) can be used with appropriate security safeguards to access and retrieve the user's data. In one embodiment, the user data stored in user data store 420 includes the user's unique identifier, the location where the user is sitting at the establishment (e.g., table number, seat number, etc.), a start time of when the user entered the establishment, the various alcohol drinks consumed and their sizes, the amount of alcohol consumed by the user, the food consumed by the user, the user's weight, gender, race/ethnicity, and a speech sample to use as a comparison in order to detect if the user's speech is slurred (indicating possible intoxication). In addition, the end time is stored of when the user checked out of the establishment.

At step 425, the user orders the first item and, at step 435, sensors included in interactive device surface 310 identify the type of item placed on the surface as well as the weight of the item. In one embodiment, small electronic tags are attached to the item (e.g., to the plate, glass, mug, etc.) and encoded with the identification of the related item (e.g., food on the plate, alcohol in the glass or mug, etc.). A determination is made, based on the identification of the item, as to whether the item is an alcoholic drink (decision 440). If the item is an alcoholic drink, then decision 440 branches to "yes" branch 445 whereupon, at step 450, the system calculates the approximate amount of alcohol in the drink. For example, if the item is a glass of wine that is 12% alcohol by volume, and the sensors weigh the item as being five ounces (after subtracting the weight of the glass), then the amount of alcohol consumed is calculated by multiplying 12% by five ounces to determine the number of ounces of alcohol in the drink. In one embodiment, the sensors weigh the items on the interactive device surface 310 in order to determine if the user consumed the entire amount of the item (e.g., the glass of wine) or only consumed a portion of the item (e.g., the user only drinks half the glass of wine). Returning to decision 440, if the item is not alcohol (e.g., a non-alcoholic drink, a plate of food, etc.), then decision 440 branches to "no" branch 455 whereupon, at step 460, the approximate amount of nutritional data consumed is calculated (e.g., grams of carbohydrates, calories, fat, etc.)

At step 465, the results of the item (alcohol or non-alcohol item) are logged in user data store 420. A determination is made as to whether there are more items ordered by the user (decision 475). When the next item is received, decision 475 branches to "yes" branch 480 whereupon processing loops back to process the next item (either an alcohol related item or a non-alcoholic item). This looping continues while the user (e.g., customer, patron, etc.) continues to order and receive items. When the user is finished (e.g., checks out), decision 475 branches to "no" branch 485 whereupon, at step 490, the ending time is logged in user data store 420.

Figure 5:
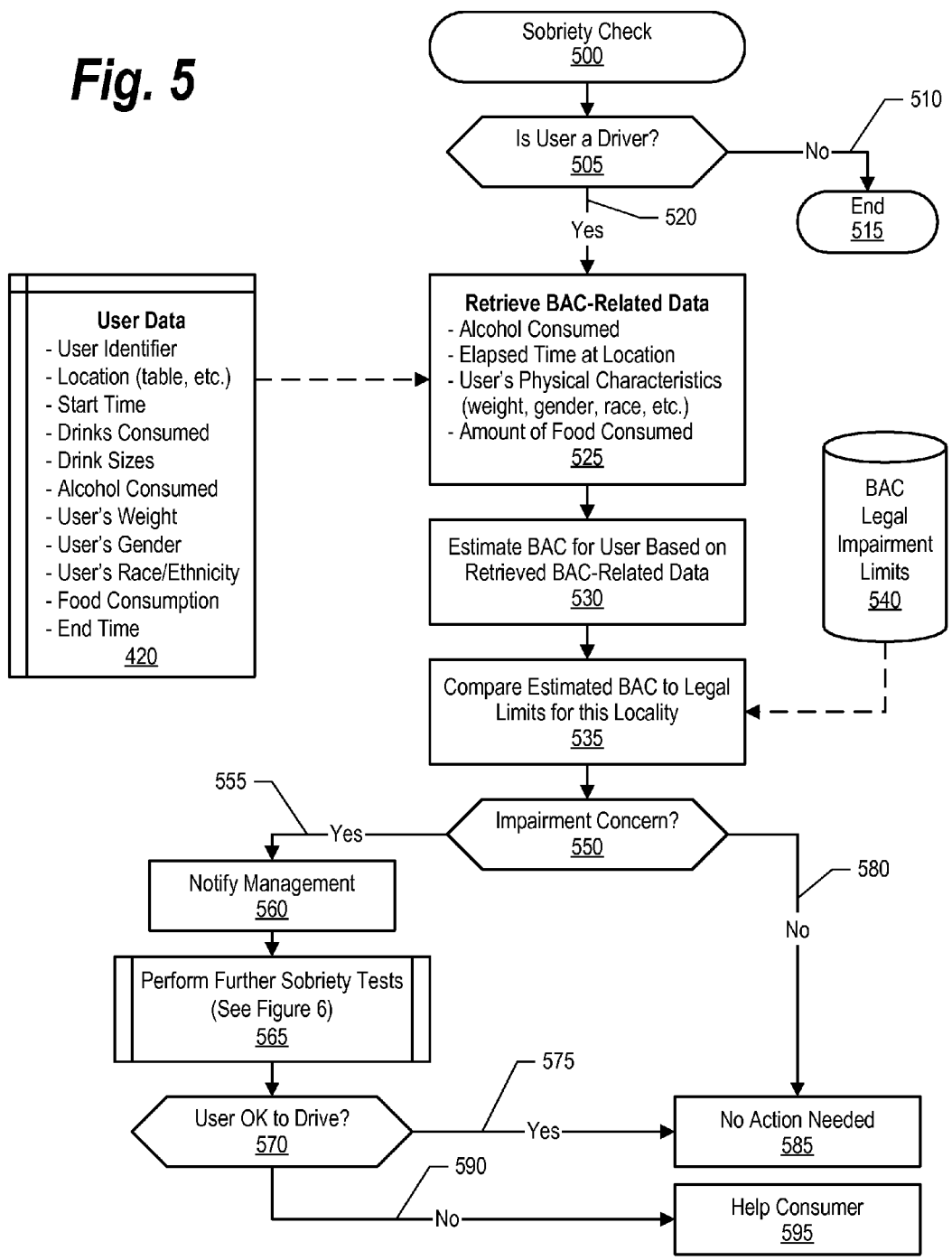
FIG. 5 is a flowchart showing steps by the interactive device to check the sobriety of a customer.

A non-invasive sobriety check is performed at predefined process 495 (see FIG. 5 and corresponding text for processing details). As will be seen in FIG. 5, the sobriety check uses the data gathered in FIG. 4 to assess whether the user is possibly impaired due to the amount of alcohol consumed.

FIG. 5 is a flowchart showing steps by the interactive device to check the sobriety of a customer in a non-invasive manner. The checking of the user's sobriety is a voluntary checking process voluntarily used by the user so that the user can assess the user's own sobriety level. The non-invasive sobriety checking commences at 500 whereupon a determination is made as to whether the user has been noted as being the driver of a vehicle (decision 505). If the user is not a driver (e.g., is taking a taxi, public transportation, or is riding with someone else, etc.), then decision 505 branches to "no" branch 510 whereupon processing ends at 515.

On the other hand, if the user is a driver, then decision 505 branches to "yes" branch 520 whereupon, at step 525, the blood-alcohol related data is retrieved from user data store 420. The blood alcohol related data includes the amount of alcohol consumed by the user, the amount of time elapsed during which the user was consuming alcohol, the user's physical characteristics (weight, gender, race, ethnicity), and the amount of non-alcohol food that was consumed by the user. At step 530, the user's estimated blood-alcohol content (BAC) is calculated using the data retrieved in step 525. At step 535, the user's estimated BAC is compared to legal limits in this locality retrieved from BAC legal limits data store 540. In one embodiment, lower limits are included in data store 540 so that further checks are made if the user's BAC is close to the legal limit. For example, if the legal limit in the jurisdiction is 0.08%, then a lower limit of 0.07% or 0.06% is also included in data store 540 in order to identify a user that is close to the impairment limits.

A determination is made as to whether an impairment concern exists for this user based upon the comparison made in step 535 (decision 550). If there is an impairment concern, then decision 550 branches to "yes" branch 555 whereupon, at step 560, an employee, such as a manager, a member of the wait-staff, etc. is notified that the user might be intoxicated in order to assist the user with getting alternate transportation as well as ensuring that if the user is intoxicated (based on the further sobriety checks performed in FIG. 6) that the user does not operate a motor vehicle and potentially subject the establishment to liability. At predefined process 565, further sobriety checks are performed using the interactive device surface 320, shown in FIGS. 3 and 5, in order to better assess whether the user is impaired. A determination is made as to whether is impaired or is OK to drive a motor vehicle (decision 570). If the user is OK to drive (not impaired), then decision 575 branches to "yes" branch 575 whereupon, at step 585, the user is allowed to drive a motor vehicle. On the other hand, if the user is impaired, then decision 570 branches to "no" branch 590 whereupon, at step 595 help is provided to the consumer (e.g., having a manager or other employee talk to the consumer and offer to call a friend or taxi cab, by using the process shown in FIG. 7, or using some other approach to help the consumer make a wise choice regarding driving while in the user's current state, etc.). Returning to decision 550, if the comparison performed at step 535 revealed that the user is not impaired to drive a motor vehicle, then decision 550 branches to "no" branch 580 whereupon, at step 585 no action is needed and the user is allowed to drive.

Figure 6:
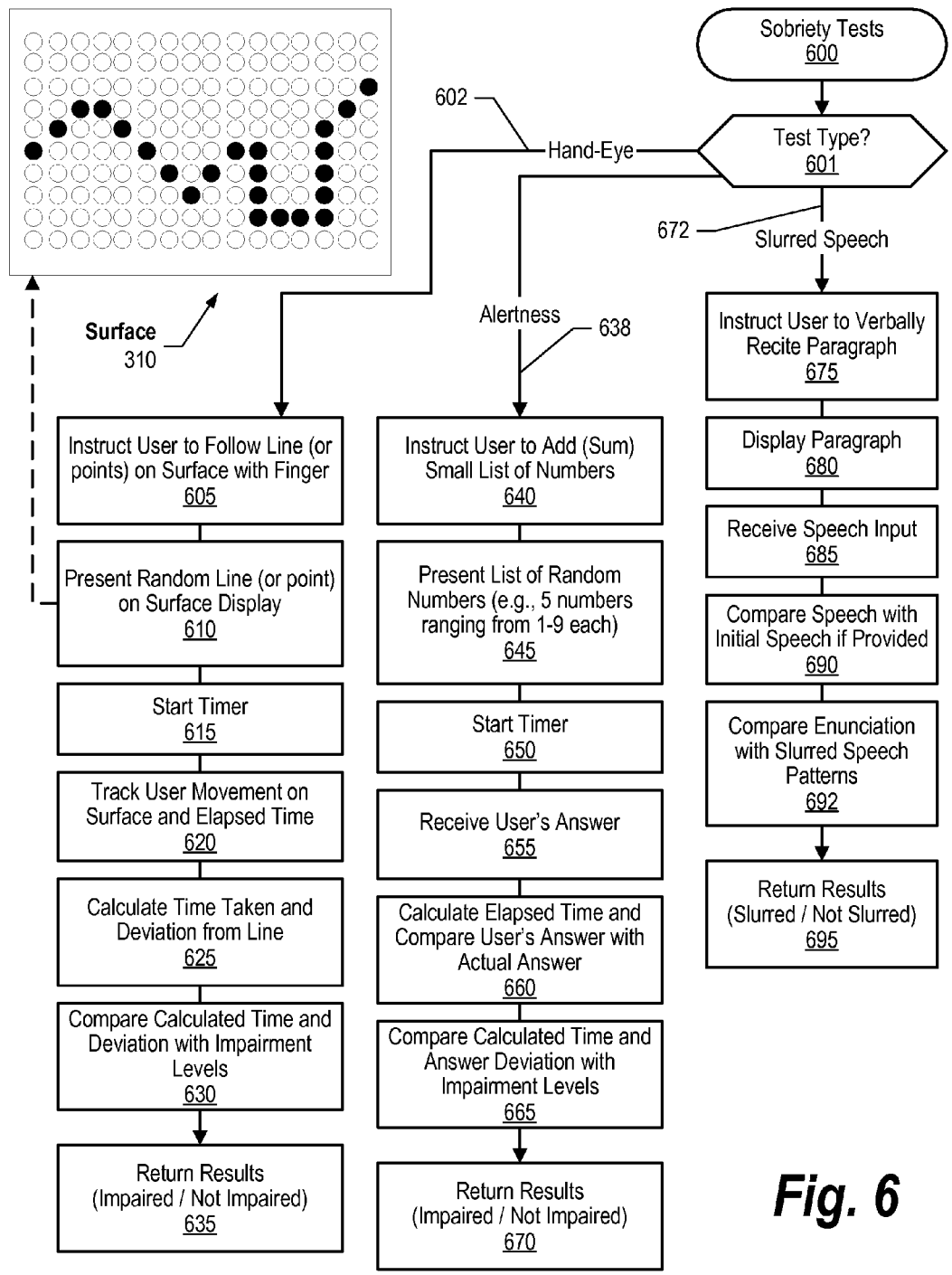
FIG. 6 is a flowchart showing steps taken by the interactive device to provide sobriety tests to the consumer.

FIG. 6 is a flowchart showing steps taken by the interactive device to provide sobriety tests to the consumer. Processing commences at 600 whereupon a determination is made as to the sobriety test that is being performed (decision 601). Note that the sobriety tests shown in FIG. 6 are voluntary tests that the user voluntarily requests to take in order to better assess whether the user sober or is instead too intoxicated to safely drive a motor vehicle. The sobriety tests shown include a hand-eye coordination test, an alertness test, and a slurred-speech test.

One or more of the sobriety tests can be performed in order to determine whether the user's ability to drive a motor vehicle appears impaired. For a hand-eye coordination test, decision 601 branches to hand-eye branch 602 whereupon, at step 605, interactive device surface 310 displays a message asking that the user attempt to follow a line that appears on surface. At step 610, a random line, or a point, is displayed on interactive device surface 310 and at step 615 a timer is started. At step 620, the user's movement is tracked on the surface along with the amount of time that elapses with the user attempting to follow the displayed line. At step 625, the interactive device calculates the amount of time it took for the user to track the displayed line as well as the user's deviation from the line (e.g., how well the user tracked the line vector as well as how well the user tracked the speed of the displayed line on surface display 310). At step 630, the calculated time and deviations from step 625 are compared with expected results. In one embodiment, expected results are grouped according to age and/or gender so that an older man's results are compared with other men of the same age, while a younger woman's results are likewise compared with expected results of women of similar ages. At step 635, the results are returned based on the comparison of the user's performance to the expected performance. As noted, this result can indicate whether the test revealed that the user's ability to operate a motor vehicle, based on their hand-eye coordination performance, is impaired or not impaired.

Returning to decision 601, another test type that can be performed is an alertness test. If an alertness test is being performed, then decision 601 branches to alertness branch 638 whereupon, at step 640 interactive device surface 310 displays a message asking that the user perform a mental process, such as adding up a short list of numbers. At step 645, the mental alertness test is displayed, such as displaying a list of five numbers each between 1 and 9 and asking the user to add the numbers in their head and provide an answer in a short amount of time. At step 650, a timer is started in the interactive device to coincide with the presentation of the mental alertness test. At step 655, the user provides an answer to the mental alertness prompt (e.g., using a verbal response, by the user typing in the answer on a virtual keypad displayed on surface 310, etc.). At step 660, the system, upon receiving the user's answer, calculates the elapsed time taken as well as the deviation from the correct answer. These figures (elapsed time and answer deviation) are compared with expected results in step 665. Once again, in one embodiment the user's age may be taken into account so that the user's performance is compared against expected performances from people with similar ages. At step 670, the results are returned based on the comparison of the user's performance to the expected performance. As noted, this result can indicate whether the test revealed that the user's ability to operate a motor vehicle, based on their alertness, is impaired or not impaired.

Returning again to decision 601, if the test type is a slurred speech test, then decision 601 branches to slurred speech branch 672 whereupon, at step 675, interactive device surface 310 displays a requests for the user to verbally recite a short paragraph. At step 680, the short paragraph is displayed on interactive device surface 310. At step 685, the interactive device receives the user's verbal input using microphones included with the interactive device. At step 690, if the user provided an initial speech sample, perhaps by reading the same short paragraph, then the initial speech sample is compared with the received verbal input of the user reciting the displayed paragraph. At step 692, the system compares the enunciation of the first speech sample with the speech sample received at step 685. If an initial speech sample was not provided by the user, then at step 692, the system compares the received enunciation with slurred speech patterns, especially on key syllables and words known to sometimes cause slurred speech in intoxicated people. At step 695, the results are returned based on the analysis and comparison of the user's verbal input that was provided in step 685. This result can indicate the level of slurred speech detected as well as whether the test revealed that the user's ability to operate a motor vehicle, based on the level of slurred speech detected, is impaired or not impaired.

Figure 7:
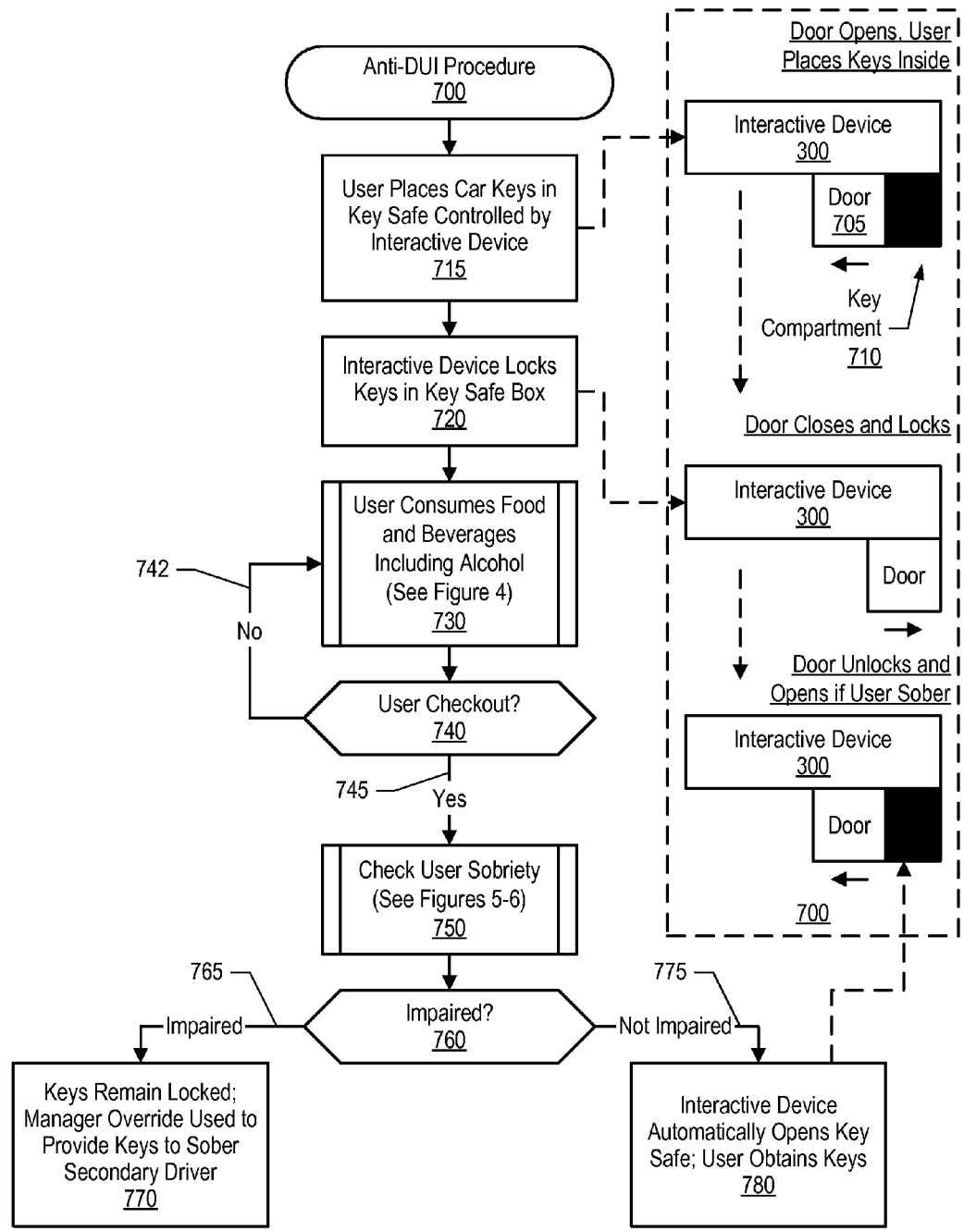
FIG. 7 is a flowchart showing steps taken to secure vehicle keys in a storage compartment controlled by the interactive device.

FIG. 7 is a flowchart showing steps taken to secure vehicle keys in a storage compartment controlled by the interactive device. Some people, when entering a bar or similar establishment, may hand over their car keys to a companion that they trust so that if the person drinks to much, their trusted companion will not return the keys and will therefore prevent the person from drinking while under the influence. FIG. 7 provides a voluntary approach that a user can use so that the interactive device serves the role of the trusted companion and will retain the person's keys in the event that the interactive device determines that the user is intoxicated. Processing commences at 700 whereupon, at step 715, the user places the keys used to operate the user's motor vehicle in a small key safe (key compartment 340), access to which is controlled by interactive device 300 that opens and closes key compartment door 705. At step 720, after the user's keys have been placed inside compartment 340, interactive device 300 locks key compartment door 705. While the keys are locked in key compartment 340, the users consumes food and beverages at the establishment (predefined process 730, see FIG. 4 and corresponding text for processing details). As described herein, some of the beverages might be alcoholic beverages that, if consumed in large enough quantities, could impair the user's ability to operate a motor vehicle. A determination is made as to whether the user is requesting to check out of the establishment (decision 740). If the user is not checking out, then decision 740 branches to "no" branch 742 which loops back process further food and drink items consumed by the user. This looping continues until the user requests to check out, at which point decision 740 branches to "yes" branch 745.

The interactive device checks the user's sobriety using non-invasive methods (predefined process 750, see FIGS. 5-6 and corresponding text for processing details). A determination is made by the interactive device as to whether the user's ability to operate a motor vehicle is impaired as a result of the sobriety checks performed at predefined process 750 (decision 760). If the user's ability to operate a motor vehicle is impaired, then decision 760 branches to impaired branch 765 whereupon, at step 770, the user's keys remain in locked key compartment 340 so that the user does not mistakenly use the keys to operate a motor vehicle. As indicated in step 770, safeguards can be established by the establishment to, for example, allow the establishment's manager to override the system and unlock compartment 340 to retrieve the keys if, for example, the manager is assured that the user is using an alternate means of transportation (e.g., a taxi, etc.), or if a different driver that has been shown to be sober using the processes described herein has agreed to drive the user's motor vehicle so that the user can safely be transported from the establishment.

One of the preferred implementations of the invention is a client application, namely, a set of instructions (program code) or other functional descriptive material in a code module that may, for example, be resident in the random access memory of the computer. Until required by the computer, the set of instructions may be stored in another computer memory, for example, in a hard disk drive, or in a removable memory such as an optical disk (for eventual use in a CD ROM) or floppy disk (for eventual use in a floppy disk drive), or downloaded via the Internet or other computer network. Thus, the present invention may be implemented as a computer program product for use in a computer. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the required method steps. Functional descriptive material is information that imparts functionality to a machine. Functional descriptive material includes, but is not limited to, computer programs, instructions, rules, facts, definitions of computable functions, objects, and data structures.

While particular embodiments of the present invention have been shown and described, it will be obvious to those skilled in the art that, based upon the teachings herein, that changes and modifications may be made without departing from this invention and its broader aspects. Therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

What is claimed is:

1. A method comprising:
   placing a vehicle key corresponding to a vehicle operated by a consumer in a lockable storage compartment, the lockable storage compartment electronically accessible by an interactive system, wherein the interactive system comprises a surface area where items are placed, one or more sensors, and the lockable storage compartment;
   in response to placing the vehicle key in the lockable storage compartment, automatically locking, by the interactive system, the lockable storage compartment;
   in response to automatically locking the lockable storage compartment, receiving one or more alcohol inputs at the interactive system, where each of the alcohol inputs corresponds to an alcoholic beverage to be consumed by the consumer, and wherein the receiving further comprises identifying, by at least one of the sensors, at least one of the alcoholic beverages in proximity to the surface area;
   calculating an estimated blood-alcohol level of the consumer based on the one or more alcohol inputs;
   comparing the estimated blood-alcohol level with one or more alcohol impairment limits retrieved from an electronic data store;
   automatically signaling an alert in response to the comparison revealing that the estimated blood-alcohol level exceeds one of the alcohol impairment limits;
   receiving, at the interactive system, a checkout signal from the consumer; and
   upon receipt of the checkout signal, sending, from the interactive system, an unlock signal to the lockable storage compartment in response to the comparison revealing that the consumer's estimated blood-alcohol level is below the alcohol impairment limits, wherein the unlock signal, when received by the lockable storage compartment, results in the lockable storage compartment automatically being unlocked.

2. The method of claim 1 further comprising:
   receiving, at the interactive system, a weight and a gender of the consumer, wherein the consumer's weight and gender are used as inputs to the calculating.

3. The method of claim 2 further comprising:
   calculating an approximate amount of alcohol in each of the alcoholic beverages to be consumed by the consumer, wherein the calculated approximate amount of alcohol is provided to the calculation of the estimated blood-alcohol level.

4. The method of claim 2 further comprising:
   retrieving, at the interactive system, a consumer identifier from the consumer, the consumer identifier uniquely identifying the consumer; and
   retrieving the weight and gender from an electronic data store wherein data regarding a plurality of consumers, including the consumer, is stored.

5. The method of claim 1 further comprising:
   receiving one or more non-alcoholic inputs at the interactive system, wherein each of the non-alcoholic inputs corresponds to a non-alcoholic food item for consumption by the consumer, wherein the non-alcoholic inputs are input to the calculation in order to reduce the estimated blood-alcohol level.

6. The method of claim 1 further comprising:
   in response to the estimated blood-alcohol level exceeding one of the alcohol impairment limits:
      presenting one or more visual sobriety tests on a visual display of the interactive system;
      receiving, at the interactive system, one or more consumer responses to each of the presented visual sobriety tests;
      retrieving one or more expected performance data corresponding to each of the presented visual sobriety tests;
      comparing the received consumer responses to the expected performance data, the comparison resulting in one or more deviation values;
      retrieving one or more impairment values corresponding to each of the presented visual sobriety tests;
      comparing the one or more deviation values to the retrieved impairment values; and
      signaling the alert in response to the comparison revealing that the consumer is impaired.

7. An information handling system that is an interactive system used to order alcoholic beverages, the information handling system comprising:
   one or more processors;
   a memory accessible by at least one of the processors;
   a display accessible by at least one of the processors;
   a surface area included in the interactive system where items are placed;
   one or more nonvolatile storage devices accessible by at least one of the processors;
   one or more sensors accessible by at least one of the processors, wherein the sensors identify the items placed on the surface area and that identify actions performed by a consumer in proximity to the surface area;
   a lockable storage compartment electronically accessible by the interactive system where a vehicle key corresponding to a vehicle operated by the consumer is placed;
   a data store stored on one of the nonvolatile storage device that includes one or more alcohol impairment limits; and
   a set of instructions which are loaded into the memory and executed by at least one of the processors in order to perform actions of:
      automatically locking the lockable storage compartment;
      in response to automatically locking the lockable storage compartment, receiving one or more alcohol inputs at the interactive system, where each of the alcohol inputs corresponds to an alcoholic beverage to be consumed by the consumer, wherein at least one of the alcohol inputs is sent by one of the sensors that identifies at least one of the alcoholic beverages in proximity to the surface area;

calculating an estimated blood-alcohol level of the consumer based on the one or more alcohol inputs;

comparing the estimated blood-alcohol level with the alcohol impairment limits retrieved from the data store;

automatically signaling an alert in response to the comparison revealing that the estimated blood-alcohol level exceeds one of the alcohol impairment limits;

receiving, at the interactive system, a checkout signal from the consumer; and upon receipt of the checkout signal, sending, from the interactive system, an unlock signal to the lockable storage compartment in response to the comparison revealing that the consumer's estimated blood-alcohol level is below the alcohol impairment limits, wherein the unlock signal, when received by the lockable storage compartment, results in the lockable storage compartment automatically being unlocked.

8. The information handling system of claim 7 wherein the instructions executed by at least one of the processors perform additional actions comprising:

receiving, at the interactive system, a weight and a gender of the consumer, wherein the consumer's weight and gender are used as inputs to the calculating.

9. The information handling system of claim 8 wherein the instructions executed by at least one of the processors perform additional actions comprising:

calculating an approximate amount of alcohol in each of the alcoholic beverages to be consumed by the consumer, wherein the calculated approximate amount of alcohol is provided to the calculation of the estimated blood-alcohol level.

10. The information handling system of claim 8 wherein the instructions executed by at least one of the processors perform additional actions comprising:

retrieving, at the interactive system, a consumer identifier from the consumer, the consumer identifier uniquely identifying the consumer; and retrieving the weight and gender from a consumer data store stored on one of the nonvolatile storage devices, wherein data regarding a plurality of consumers, including the consumer, is stored.

11. The information handling system of claim 7 wherein the instructions executed by at least one of the processors perform additional actions comprising:

receiving one or more non-alcoholic inputs at the interactive system, wherein each of the non-alcoholic inputs corresponds to a non-alcoholic food item for consumption by the consumer, wherein the non-alcoholic inputs are input to the calculation in order to reduce the estimated blood-alcohol level.

12. The information handling system of claim 7 wherein the instructions executed by at least one of the processors perform additional actions comprising:

in response to the estimated blood-alcohol level exceeding one of the alcohol impairment limits:

presenting one or more visual sobriety tests on a visual display of the interactive system;

receiving, at the interactive system, one or more consumer responses to each of the presented visual sobriety tests;

retrieving one or more expected performance data corresponding to each of the presented visual sobriety tests;

comparing the received consumer responses to the expected performance data, the comparison resulting in one or more deviation values;

retrieving one or more impairment values corresponding to each of the presented visual sobriety tests;

comparing the one or more deviation values to the retrieved impairment values; and signaling the alert in response to the comparison revealing that the consumer is impaired.

13. A computer program product stored in a non-transitory computer readable medium, comprising functional descriptive material that, when executed by an information handling system, causes the information handling system to perform actions that include:

automatically locking, by an interactive system, a lockable storage compartment, the lockable storage compartment electronically accessible by the interactive system, wherein the locking occurs in response to a vehicle key corresponding to a vehicle operated by a consumer being placed in the lockable storage compartment, wherein the interactive system comprises a surface area where items are placed, one or more sensors, and the lockable storage compartment;

in response to automatically locking the lockable storage compartment, receiving one or more alcohol inputs at the interactive system, where each of the alcohol inputs corresponds to an alcoholic beverage to be consumed by the consumer, and wherein the receiving further comprises identifying, by at least one of the sensors, at least one of the alcoholic beverages in proximity to the surface area;

calculating an estimated blood-alcohol level of the consumer based on the one or more alcohol inputs;

comparing the estimated blood-alcohol level with one or more alcohol impairment limits retrieved from an electronic data store;

automatically signaling an alert in response to the comparison revealing that the estimated blood-alcohol level exceeds one of the alcohol impairment limits;

receiving, at the interactive system, a checkout signal from the consumer; and upon receipt of the checkout signal, sending, from the interactive system, an unlock signal to the lockable storage compartment in response to the comparison revealing that the consumer's estimated blood-alcohol level is below the alcohol impairment limits, wherein the unlock signal, when received by the lockable storage compartment, results in the lockable storage compartment automatically being unlocked.

14. The computer program product of claim 13 further comprising functional descriptive material that causes the information handling system to perform additional actions that include:

receiving, at the interactive system, a weight and a gender of the consumer, wherein the consumer's weight and gender are used as inputs to the calculating.

15. The computer program product of claim 14 further comprising functional descriptive material that causes the information handling system to perform additional actions that include:

calculating an approximate amount of alcohol in each of the alcoholic beverages to be consumed by the consumer, wherein the calculated approximate amount of alcohol is provided to the calculation of the estimated blood-alcohol level.

16. The computer program product of claim 14 further comprising functional descriptive material that causes the information handling system to perform additional actions that include:
   retrieving, at the interactive system, a consumer identifier from the consumer, the consumer identifier uniquely identifying the consumer; and
   retrieving the weight and gender from an electronic data store wherein data regarding a plurality of consumers, including the consumer, is stored.

17. The computer program product of claim 13 further comprising functional descriptive material that causes the information handling system to perform additional actions that include:
   in response to the estimated blood-alcohol level exceeding one of the alcohol impairment limits:
      presenting one or more visual sobriety tests on a visual display of the interactive system;
      receiving, at the interactive system, one or more consumer responses to each of the presented visual sobriety tests;
      retrieving one or more expected performance data corresponding to each of the presented visual sobriety tests;
      comparing the received consumer responses to the expected performance data, the comparison resulting in one or more deviation values;
      retrieving one or more impairment values corresponding to each of the presented visual sobriety tests;
      comparing the one or more deviation values to the retrieved impairment values; and
      signaling the alert in response to the comparison revealing that the consumer is impaired.

* * * * *